United States Patent
Winarta et al.

(12)

(10) Patent No.: US 6,287,451 B1
(45) Date of Patent: Sep. 11, 2001

(54) DISPOSABLE SENSOR AND METHOD OF MAKING

(76) Inventors: Handani Winarta, 18 Hyacinth Dr., Nashua, NH (US) 03062; Xiaohua Cai, 19 McCulloch St., Needham, MA (US) 02494; Fung Seto, 31 Pratt Dr., Newton, MA (US) 02465; Chung Chang Young, 145 Buckskin Dr., Weston, MA (US) 02193

( * ) Notice: Subject to any disclaimer, the term of this patent is extended or adjusted under 35 U.S.C. 154(b) by 0 days.

(21) Appl. No.: 09/324,443

(22) Filed: Jun. 2, 1999

(51) Int. Cl.[7] .................................................. G01N 27/26
(52) U.S. Cl. ...................... 205/777.5; 205/792; 204/403; 216/52
(58) Field of Search ................................... 204/403, 412; 205/777.5, 775, 792; 216/52; 438/460, 462, 463

(56) References Cited

U.S. PATENT DOCUMENTS

| | | |
|---|---|---|
| 3,838,033 | 9/1974 | Mindt et al. . |
| 3,979,274 | 9/1976 | Newman . |
| 4,053,381 | 10/1977 | Hamblen et al. . |
| 4,133,735 | 1/1979 | Afromowitz . |
| 4,137,495 | 1/1979 | Brown . |
| 4,184,936 | 1/1980 | Paul et al. . |
| 4,185,131 | 1/1980 | Goller et al. . |
| 4,206,755 | * 6/1980 | Klein ........................................ 604/28 |
| 4,224,125 | 9/1980 | Nakamura et al. . |
| 4,225,410 | 9/1980 | Pace . |
| 4,233,029 | 11/1980 | Colombus . |
| 4,273,639 | 6/1981 | Gottermeier . |
| 4,301,414 | 11/1981 | Hill et al. . |

(List continued on next page.)

FOREIGN PATENT DOCUMENTS

| | | |
|---|---|---|
| 0096095 | 12/1983 | (EP) . |
| 0121385 | 10/1984 | (EP) . |
| 0136362 | 4/1985 | (EP) . |
| 0170375 | 2/1986 | (EP) . |
| 0255291 | 2/1988 | (EP) . |
| 41111879 A | * 4/1999 | (JP) . |
| 8803270 | 5/1988 | (WO) . |

OTHER PUBLICATIONS

JPAB abstract of Miyamoto et al.. (JP 411118794A), Apr. 1999.*
WO 98/35225 PCT Application, Aug. 13, 1998, Adam Heller et al.
WO 98/55856 PCT Application, Dec. 10, 1998, Stephen Williams et al.

*Primary Examiner*—T. Tung
*Assistant Examiner*—Alex Noguerola
(74) *Attorney, Agent, or Firm*—Robert R. DeLeault, Esq.; Mesmer & DeLeault, PLLC (57) ABSTRACT

A disposable electrode strip for testing a fluid sample including a laminated strip with a first and second end, a reference electrode embedded in the laminated strip proximate to the first end, at least two working electrodes embedded in the laminated strip proximate to the first end and the reference electrode, an open path for receiving a fluid sample beginning from the first end and being sufficiently long to expose the reference electrode and the working electrodes to the fluid sample, and conductive contacts located at the second end of the laminated strip. The laminated strip has a base layer with a conductive coating, a reagent holding layer, a channel forming layer and a cover. One of the working electrodes contains a reagent substantially similar to the reagent of the reference electrode and a second working electrode contains a reagent having an enzyme.

42 Claims, 8 Drawing Sheets

U.S. PATENT DOCUMENTS

| | | |
|---|---|---|
| 4,303,887 | 12/1981 | Hill et al. . |
| 4,310,399 | 1/1982 | Columbus . |
| 4,356,074 | 10/1982 | Johnson . |
| 4,376,689 | 3/1983 | Nakamura et al. . |
| 4,413,407 | 11/1983 | Columbus . |
| 4,418,148 | 11/1983 | Oberhardt . |
| 4,454,007 | 6/1984 | Pace . |
| 4,469,110 | 9/1984 | Slama . |
| 4,473,457 | 9/1984 | Columbus . |
| 4,490,216 | 12/1984 | McConnell . |
| 4,502,938 | 3/1985 | Covington et al. . |
| 4,545,382 | 10/1985 | Higgins et al. . |
| 4,591,550 | 5/1986 | Hafeman et al. . |
| 4,654,127 | 3/1987 | Baker et al. . |
| 4,897,173 | 1/1990 | Nankai et al. . |
| 4,900,405 | 2/1990 | Otagawa et al. . |
| 5,120,420 | 6/1992 | Nankai et al. . |
| 5,141,868 | 8/1992 | Shanks et al. . |
| 5,185,256 | 2/1993 | Nankai et al. . |
| 5,264,103 | 11/1993 | Yoshioka et al. . |
| 5,266,179 | 11/1993 | Nankai et al. . |
| 5,288,636 | 2/1994 | Pollman et al. . |
| 5,354,447 | 10/1994 | Uenoyama et al. . |
| 5,382,346 | 1/1995 | Uenoyama et al. . |
| 5,395,504 | 3/1995 | Saurer et al. . |
| 5,437,999 | 8/1995 | Diebold et al. . |
| 5,496,453 | 3/1996 | Uenoyama et al. . |
| 5,508,171 | 4/1996 | Walling et al. . |
| 5,509,410 | 4/1996 | Hill et al. . |
| 5,628,890 | 5/1997 | Carter et al. . |
| 5,682,884 | 11/1997 | Hill et al. . |
| 5,708,247 | 1/1998 | McAleer et al. . |
| 5,727,548 | 3/1998 | Hill et al. . |
| 5,755,953 | 5/1998 | Henning et al. . |
| 5,759,364 | 6/1998 | Charlton et al. . |
| 5,762,770 | 6/1998 | Pritchard et al. . |
| 5,820,551 | 10/1998 | Hill et al. . |
| 5,997,817 | 12/1999 | Crismore et al. . |

* cited by examiner

DISPOSABLE SENSOR AND METHOD OF MAKING

BACKGROUND OF THE INVENTION

1. Field of the Invention

The present invention relates generally to electrochemical sensors that can be used for the quantification of a specific component or analyte in a liquid sample. Particularly, this invention relates to a new and improved electrochemical sensor and to a new and improved method of fabricating electrochemical sensors. More particularly, this invention relates to a disposable electrochemical sensor that is inexpensive to manufacture. Even more particularly, this invention relates to a disposable electrochemical sensor that gives accurate readings in the presence of interferants and varying red blood cells (hematocrit). Still even more particularly, this invention relates to disposable electrochemical sensors which are used for performing electrochemical assays for the accurate determination of analytes in physiological fluids.

2. Description of the Prior Art

Biosensors have been known for more than three decades. They are used to determine concentrations of various analytes in fluids. Of particular interest is the measurement of blood glucose. It is well known that the concentration of blood glucose is extremely important for maintaining homeostasis. Products that measure fluctuations in a person's blood sugar, or glucose levels have become everyday necessities for many of the nation's millions of diabetics. Because this disorder can cause dangerous anomalies in blood chemistry and is believed to be a contributor to vision loss and kidney failure, most diabetics need to test themselves periodically and adjust their glucose level accordingly, usually with insulin injections. If the concentration of blood glucose is below the normal range, patients can suffer from unconsciousness and lowered blood pressure which may even result in death. If the blood glucose concentration is higher than the normal range, the excess blood glucose can result in synthesis of fatty acids and cholesterol, and in diabetics, coma. Thus, the measurement of blood glucose levels has become a daily necessity for diabetic individuals who control their level of blood glucose by insulin therapy.

Patients who are insulin dependent are instructed by doctors to check their blood-sugar levels as often as four times a day. To accommodate a normal life style to the need of frequent monitoring of glucose levels, home blood glucose testing was made available with the development of reagent strips for whole blood testing.

One type of blood glucose biosensors is an enzyme electrode combined with a mediator compound which shuttles electrons between the enzyme and the electrode resulting in a measurable current signal when glucose is present. The most commonly used mediators are potassium ferricyanide, ferrocene and its derivatives, as well as other metal-complexes. Many sensors based on this second type of electrode have been disclosed. Examples of this type of device are disclosed in the following patents.

U.S. Pat. No. 5,628,890 (1997, Carter et al.) Disclosed an electrode strip having an electrode support, a reference or counter electrode disposed on the support, a working electrode spaced from the reference or counter electrode on the support, a covering layer defining an enclosed space over the reference and working electrodes and having an aperture for receiving a sample into the enclosed space, and a plurality of mesh layers interposed in the enclosed space between the covering layer and the support. The covering layer has a sample application aperture spaced from the electrodes. The working electrode includes an enzyme capable of catalyzing a reaction involving a substrate for the enzyme and a mediator capable of transferring electrons between the enzyme-catalyzed reaction and the working electrode.

This device proposes to reduce the effect of hematocrit on the sensor readings. According to the disclosure, this results from the downstream spacing of the reference electrode relative to the working electrode in combination with the thin layer of the sample solution created by the mesh layers.

U.S. Pat. No. 5,708,247 (1998, McAleer et al.) Disclosed a disposable glucose test strip having a substrate, a reference electrode, a working electrode, and a means for making an electrical connection. The working electrode has a conductive base layer and a coating layer disposed over the conductive base layer. The coating layer is a filler having both hydrophobic and hydrophilic surface regions which form a network, an enzyme and a mediator.

U.S. Pat. No. 5,682,884 (1997, Hill et al.) Disclosed a strip electrode with screen printing. The strip has an elongated support which includes a first and second conductor each extending along the support. An active electrode, positioned to contact the liquid mixture and the first conductor, has a deposit of an enzyme capable of catalyzing a reaction and an electron mediator. A reference electrode is positioned to contact the mixture and the second conductor.

U.S. Pat. No. 5,759,364 (1998, Charlton et al.) Disclosed an electrochemical biosensor having an insulating base plate bearing an electrode on its surface which reacts with an analyte to produce mobile electrons. The base plate is mated with a lid of deformable material which has a concave area surrounded by a flat surface so that when mated to the base plate there is formed a capillary space into which a fluid test sample can be drawn. The side of the lid facing the base is coated with a polymeric material which serves to bond the lid to the base plate and to increase the hydrophilic nature of the capillary space.

U.S. Pat. No. 5,762,770 (1998, Pritchard et al.) Disclosed an electrochemical biosensor test strip that has a minimum volume blood sample requirement of about 9 microliters. The test strip has a working and counter electrodes that are substantially the same size and made of the same electrically conducting material placed on a first insulating substrate. Overlaying the electrodes is a second insulating substrate which includes a cutout portion that forms a reagent well. The cutout portion exposes a smaller area of the counter electrode than the working electrode. A reagent for analysis of an analyte substantially covers the exposed areas of the working and counter electrodes in the reagent well. Overlaying the reagent well and affixed to the second insulating substrate is a spreading mesh that is impregnated with a surfactant.

U.S. Pat. No. 5,755,953 (1998, Henning et al.) Disclosed an reduced-interference biosensor. The device generally comprises an electrode used to electrochemically measure the concentration of an analyte of interest in a solution. The device includes a peroxidase enzyme covalently bound to microparticle carbon and retained in a matrix in intimate contact with the electrode. According to this disclosure, it is the enzyme/microparticle carbon of the device which provides a composition which is displays little sensitivity to known interfering substances.

U.S. Pat. No. 5,120,420 (1992, Nankai et al.) Disclosed a biosensor with a base board having an electrode system mainly made of carbon, an insulating layer, a reaction layer containing an enzyme layer thereon, a spacer and a cover. The spacer creates a channel with an inlet and an outlet for holding a sample.

However, the prior art devices suffer from various shortcomings. One of these shortcomings is interference with biosensor readings caused by other substances in the sample fluid which can oxidize at the same potential. Prevalent among these are ascorbic acid, uric acid and acetaminophen. As these and other interfering substances oxidize, the current resulting from their oxidation is added to and indistinguishable from the current resulting from the oxidation of the blood analyte being measured. An error therefore results in the quantification of the blood analyte.

Another shortcoming is the interference caused by red blood cells (the hematocrit effect). This interference tends to cause an artificially high response rate for low hematocrit levels and, conversely, an artificially low response rate for high hematocrit levels.

Additional shortcomings of the prior art devices are that they have a more limited linear range and require a relatively large quantity of sample volume. Further, they require a relatively longer waiting time for development of a steady-state response before a reading can be achieved. Each of these shortcomings may, either individually or when combined with one or more of the other shortcomings, contribute to erroneous measurement readings during analysis. Preliminary tests performed by the inventors of the present invention have shown that the prior art which claims to reduce the effect of hematocrit on glucose readings, were limited to and worked only in lower glucose concentrations.

Because of the importance of obtaining accurate glucose readings, it would be highly desirable to develop a reliable and user-friendly electrochemical sensor which does not have all of the drawbacks mentioned above. Therefore what is needed is an electrochemical sensor that incorporates an interference-correcting electrode to minimize the interference caused by oxidizable substances present in the sample fluid. What is further needed is an electrochemical sensor whose response is substantially independent of the hematocrit of the sample fluid. What is still further needed is an electrochemical sensor which requires less sample volume than previously required by the prior art. Yet, what is still further needed is an electrochemical sensor which has a wide linear measurement range; that is, a sensor having a reduced or negligible interference effect and useable over a wider glucose concentration.

SUMMARY OF THE INVENTION

It is an object of the present invention to provide an improved electrochemical sensor which combines an enzyme and a mediator. It is a further object of the present invention to provide an electrochemical sensor that incorporates an interference-correcting electrode to minimize the interference caused by oxidizable substances present in the sample fluid. It is a further object of the present invention to provide an electrochemical sensor whose response is substantially independent of the hematocrit levels of the sample fluid. It is still another object of the present invention to provide an electrochemical sensor which requires less sample volume than previously required by the prior art. It is yet another object of the present invention to provide an electrochemical sensor which has a wide linear measurement range.

The present invention achieves these and other objectives by providing an electrochemical sensor which requires a smaller sample size and compensates for interference from oxidizable species in the sample and from varying hematocrit levels. The present invention has a laminated, elongated body having a sample fluid channel connected between an opening on one end of the laminated body and a vent hole spaced from the opening. Within the fluid channel lies at least two working electrodes and a reference electrode. The arrangement of the two working electrodes and the reference electrode is not important for purposes of the results obtained from the electrochemical sensor. The working electrodes and the reference electrode are each in electrical contact with separate conductive conduits, respectively. The separate conductive conduits terminate and are exposed for making an electrical connection to a reading device on the end opposite the open channel end of the laminated body.

The laminated body has a base insulating layer made from a plastic material. Several conductive conduits are delineated on the base insulating layer. The conductive conduits may be deposited on the insulating layer by screen printing, by vapor deposition, or by any method that provides for a conductive layer which adheres to the base insulating layer. The conductive conduits may be individually disposed on the insulating layer, or a conductive layer may be disposed on the insulating layer followed by etching/scribing the required number of conductive conduits. The etching process may be accomplished chemically, by mechanically scribing lines in the conductive layer, by using a laser to scribe the conductive layer into separate conductive conduits, or by any means that will cause a break between and among the separate conductive conduits required by the present invention. The preferred conductive coatings are gold film or a tin oxide/gold film composition. It should be pointed out that although the same electrically conducting substance (gold film or tin oxide/gold film) after scoring is used as conducting material for both working electrodes and the reference electrode, this material itself cannot function as a reference electrode. To make the reference electrode work, there must be a redox reaction (e.g., $Fe(CN)_6^{3-} + e^- \rightarrow Fe(CN)_6^{4-}$) at the electrically conducting material when a potential is applied. Therefore, a redox mediator must be present at the conducting material used for the reference electrode.

On top of the base insulating layer and the conductive conduits, the laminated body has a first middle insulating layer containing cutouts for at least two working electrodes and a reference electrode. One of the working electrodes and reference electrode may share the same cutout, provided that the electrode material (described later) disposed in the cutout is scored to isolate the working electrode from the reference electrode. Where three cutouts are used, each cutout corresponds to and exposes a small portion of a single conductive conduit. The cutouts for the working electrodes are substantially the same size. The cutout for the reference electrode may be the same or different size as the cutouts for the working electrodes. The placement of all of the cutouts are such that they will all co-exist within the sample fluid channel described above. This first middle insulating layer is also made of an insulating dielectric material, preferably plastic, and may be made by die cutting the material mechanically or with a laser and then fastening the material to the base layer. An adhesive, such as a pressure-sensitive adhesive, may be used to secure the first middle insulating layer to the base layer. Adhesion may also be accomplished by ultrasonically bonding the first middle layer to the base layer. The first middle insulating layer may also be made by screen printing the first middle insulating layer over the base layer.

The thickness of the first middle layer must be of sufficient thickness for loading a sufficient amount of electrode material for use as an electrochemical sensor. Each cutout contains electrode material. The electrode material has a redox mediator with at least one of a stabilizer, a binder, a surfactant, and a buffer. At least one of the cutouts also contains an enzyme capable of catalyzing a reaction involving a substrate for the enzyme. The redox mediator is capable of transferring electrons between the enzyme-catalyzed reaction and the working electrode.

The laminated body also has a second middle insulating layer on top of the first middle layer. The second middle layer is also made of a plastic insulating material and creates the sample fluid channel of the laminated body. It contains a U-shaped cutout on one end which overlays the cutouts on the first middle layer with the open end corresponding to the open end of the laminated body described earlier.

The laminated body of the present invention has a top layer with a vent opening. The vent opening is located such that at least a portion of the vent opening overlays the bottom of the U-shaped cutout of the second middle insulating layer. The vent allows air within the sample fluid channel to escape as the sample fluid enters the open end of the laminated body. The sample fluid generally fills the sample fluid channel by capillary action. In small volume situations, the extent of capillary action is dependent on the hydrophobic/hydrophilic nature of the surfaces in contact with the fluid undergoing capillary action. This is also known as the wetability of the material. Capillary forces are enhanced by either using a hydrophilic insulating material to form the top layer, or by coating at least a portion of one side of a hydrophobic insulating material with a hydrophilic substance in the area of the top layer that faces the sample fluid channel between the open end of the laminated body and the vent opening of the top layer. It should be understood that an entire side of the top layer may be coated with the hydrophilic substance and then bonded to the second middle layer.

The insulating layers of the laminated body may be made from any dielectric material. The preferred material is a plastic material. Examples of acceptable compositions for use as the dielectric material are polyvinyl chloride, polycarbonate, polysulfone, nylon, polyurethane, cellulose nitrate, cellulose propionate, cellulose acetate, cellulose acetate butyrate, polyester, acrylic, and polystyrene.

The number of cutouts in the first middle layer can be one, two and three or more. To use only one cutout, the single cutout must expose portions of two conductive conduits. The electrode material within the single cutout is scored in the middle to separate it into two parts; one acting as the working electrode and the other acting as the reference electrode. Such an arrangement allows for testing a smaller sample volume compared to two or three cutout embodiment. However, this embodiment lacks the interference and hematocrit correction features of the other embodiments.

An embodiment having two cutouts is an alternative to the single cutout version. It has one cutout serving as the working electrode and the other one serving as a reference electrode. Another embodiment of the two cutout version combines the features of making the single cutout with that of the two cutout version. One of the cutouts containing electrode material is scored into two parts, one part serving as a first working electrode and the second part serving as the reference electrode. The second cutout serves as a second working electrode. Such a design is an alternative embodiment of the preferred embodiment of the present invention. This version of the two-cutout embodiment has the interference and hematocrit correction features but also allows for measuring an even smaller sample volume than that of the three-cutout embodiment.

In the three-cutout embodiment, two cutouts contain material for the working electrodes (W1 and W2) and one for the reference electrode (R). W2 further contains the enzyme capable of catalyzing a substrate of the enzyme. The three electrodes are positioned and sized in such a way that the resistance of the fluid sample could be precisely measured and the possible carry-over from W2 could be minimized. The possible electrode arrangements within the sample fluid channel may be W1-W2-R, W1-R-W2, R-W1-W2, W2-W1-R, W2-R-W1, or R-W2-W1 with the arrangement listed as the arrangement of electrodes would appear from the open end of the laminated body to the vent opening. The preferred position was found to be W1-R-W2; that is, as the sample fluid entered the open end of the laminated body, the fluid would cover W1 first, then R, then W2. The preferred position allows for the precise measurement of blood sample resistance. This is necessary for good correlation between the resistance and hematocrit level in the blood sample.

As mentioned earlier, oxidizable interferants such as ascorbic acid, uric acid and acetaminophen, to name a few, cause inaccurate readings in the output of an electrochemical biosensor. The present invention negates this effect by subtracting the current response at W1 (first working electrode) from the current response from W2 (second working electrode) to calculate the enzyme concentration in the sample fluid. This is achieved by maintaining the surface area of W1 substantially equal to the surface area of W2. Also important is the composition of the reagents disposed on W1 and W2. The reagents are designed to have a minimal effect on the response of the interferences which also contributes to the accuracy of the analyte measurement.

The hematocrit interference is reduced by using a two-step process. First, the resistance (r-value) between W1 (first working electrode) and R (reference electrode) is measured. The r-value is then used to estimate the hematocrit level in the sample fluid. The following equation represents this relationship:

$$r = k_1/(1-H) \qquad \text{Eq. (1)}$$

where r is resistance value measured in Ohms or Kilo-Ohms

H is hematocrit level $k_1$ is a constant equal to 4.6 (r measured in Kilo-Ohms)

Second, the hematocrit level value is then used to mathematically correct the enzyme concentration reading obtained from above. The following equation represents the calculation performed using the calculated hematocrit level from Eq. (1):

$$C_{corr} = C_{mea}/(k_2 + k_3 C_{mea} + (k_4 + k_5 C_{mea})(1-H)) \qquad \text{Eq. (2)}$$

where $C_{corr}$ is the corrected analyte concentration $C_{mea}$ is the measured analyte concentration $k_2$ is a constant equal to 1.03

$k_3$ is a constant equal to $-0.003$ $k_4$ is a constant equal to $-0.1$ $k_5$ is a constant equal to 0.0054

H is the calculated hematocrit level from Eq. (1)

The constant values above have been determined for the preferred embodiment of the present invention. Varying the surface area of the electrode areas and the formulations of the reagents may require one skilled in the art to calculate new values for constants $k_1$–$k_5$ in order to more accurately determine corrected glucose concentration.

All of the advantages of the present invention will be made clearer upon review of the detailed description, drawings and appended claims.

DETAILED DESCRIPTION OF THE PREFERRED EMBODIMENT

Figure 1:
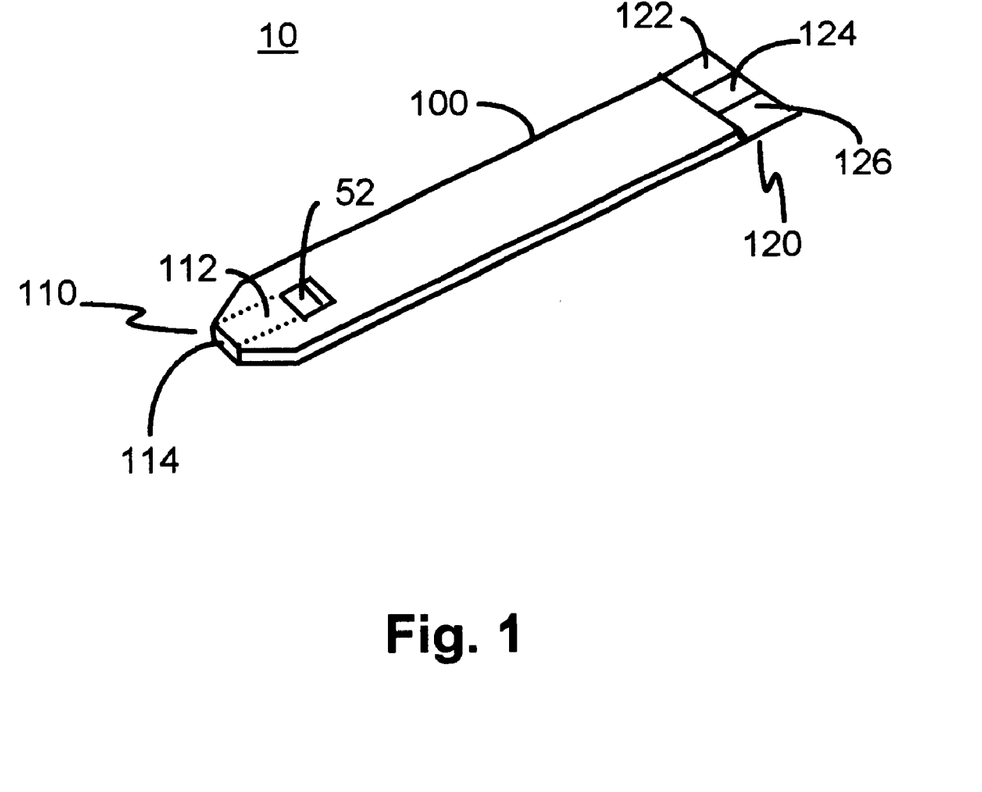
FIG. 1 is a perspective view of the present invention showing the open end, the vent and the electrical contact points of the laminated body.

The preferred embodiment of the present invention is illustrated in FIGS. 1–6. FIG. 1 shows a sensor 10 of the present invention. Sensor 10 has a laminated body 100, a fluid sampling end 110, an electrical contact end 120, and a vent opening 52. Fluid sampling end 110 includes a sample fluid channel 112 between a sampling end aperture 114 and vent opening 52. Electrical contact end 120 has at least three discreet conductive contacts 122, 124 and 126.

Figure 2:
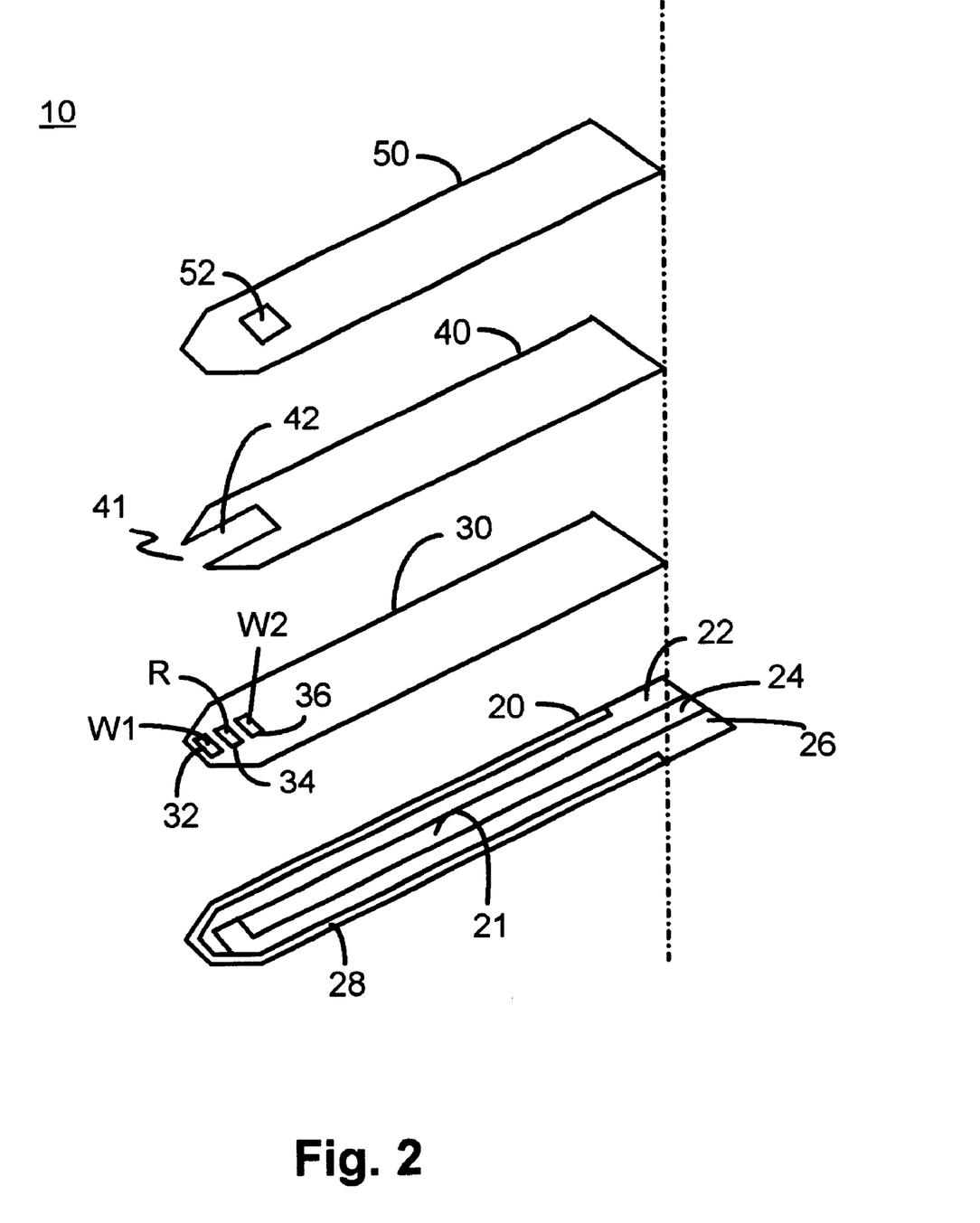
FIG. 2 is an exploded, perspective view of the present invention showing the various layers of the laminated body.

Referring now to FIG. 2, laminated body 100 is composed of a base insulating layer 20, a first middle layer 30, a second middle layer 40, and a top layer 50. All layers are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, acrylic and polystyrene. Base insulating layer 20 has a conductive layer 21 on which is delineated a first conductive conduit 22, a second conductive conduit 24 and a third conductive conduit 26. Conductive conduits 22, 24 and 26 may be formed by scribing or scoring the conductive layer 21 as illustrated in FIG. 2 or by silk-screening the conductive conduits 22, 24 and 26 onto base layer 20. Scribing or scoring of conductive layer 21 may be done by mechanically scribing the conductive layer 21 sufficiently to create the three independent conductive conduits 22, 24 and 26. The preferred scribing or scoring method of the present invention is done by using a carbon dioxide ($CO_2$) laser, a YAG laser or an eximer laser. An additional scoring line 28 (enlarged and not to scale; for illustrative purposes only) may be made, but is not necessary to the functionality of sensor 10, along the outer edge of base layer 20 in order to avoid potential static problems which could give rise to a noisy signal. Conductive layer 21 may be made of any electrically conductive material, preferably gold or tin oxide/gold. A useable material for base layer 20 is a tin oxide/gold polyester film (Cat. No. FM-1) or a gold polyester film (Cat. No. FM-2) sold by Courtaulds Performance Films, Canoga Park, Calif.

First middle layer 30 has a first electrode cutout 32 which exposes a portion of first conductive conduit 22, a second electrode cutout 34 which exposes a portion of second conductive conduit 24 and a third electrode cutout 36 which exposes a portion of third conductive conduit 26. First layer 30 is made of a plastic material, preferably a medical grade one-sided tape available from Adhesive Research, Inc., of Glen Rock, Pa. Acceptable thickness of the tape for use in the present invention are in the range of about 0.003 in. (0.76 mm) to about 0.005 in. (0.127 mm). One such tape, Arcare®7815, was preferred because of its ease of handling and it showed good performance in terms of its ability to hold a sufficient quantity of chemical reagents and to promote a favorable blood flood speed (capillary action) through sample fluid channel 112 of sensor 10. It should be understood that the use of a tape is not required. A plastic insulating layer may be coated with a pressure sensitive adhesive, or may be ultrasonically-bonded to base layer 20, or may be silk-screened onto base layer 20 to achieve the same results as using the polyester tape mentioned.

The three cutouts 32, 34 and 36 define electrode areas W1, R and W2, respectively, and hold chemical reagents forming two working electrodes and one reference electrode. Typically, electrode area R must be loaded with a redox reagent or mediator to make the reference electrode function. If R is not loaded with a redox reagent or mediator, working electrodes W1 and W2 will not work. Electrode areas W1 and R are loaded preferably with the same chemical reagent to facilitate the resistance measurement described earlier. The reagents preferably contain an oxidized form of a redox mediator, a stabilizer, a binder, a surfactant, and a buffer. Typically, the redox mediator may be at least one of ferrocene, potassium ferricyanide and other ferrocene derivatives. The preferred stabilizer is polyethylene glycol, the preferred binder is methyl cellulose, the preferred surfactant is t-octylphenoxypolyethoxyethanol, and the preferred buffer is a citrate buffer. Electrode area W2 is preferably loaded with the same chemical reagents loaded into electrode areas W1 and R but with the addition of an enzyme capable of catalyzing a reaction involving a substrate for the enzyme or a substrate catalytically reactive with an enzyme and a mediator capable of transferring electrons transferred between the enzyme-catalyzed reaction and the working electrode to create a current representative of the activity of the enzyme or substrate and representative of the compound.

The cutouts and electrode areas of first layer 30 are positioned relative to each other and to the flow of the sample fluid in sample fluid channel 112 such that the resistance of the sample fluid may be precisely measured and the possible carryover from electrode area W2 to electrode area W1 could be minimized. Using fluid sample end 110 of sensor 10 as a reference point, the arrangements of the electrode areas could be W1-W2-R, W1-R-W2, R-W1-W2, W2-W1-R, W2-R-W1, or R-W2-W1. The preferred position was found to be W1-R-W2.

Second middle layer 40 has a U-shaped channel cutout 42 located at second layer sensor end 41. The length of channel cutout 42 is such that when second middle layer 40 is layered on top of first middle layer 30, electrode areas W1, W2 and R are within the space defined by channel cutout 42.

The thickness of second middle layer 40 was found to be critical for the speed of the sample fluid flow into sample fluid channel 112, which is filled by capillary action of the sample fluid.

Top layer 50, which is placed over second middle layer 40, has a vent opening 52 spaced from fluid sample end 110 of sensor 10 to insure that sample fluid in fluid channel 112 will completely cover electrode areas W1, W2 and R. Vent opening 52 is placed in top layer 50 so that it will align somewhat with the bottom of channel cutout 42 of second middle layer 40. Preferably, vent opening 52 will expose a portion of and partially overlay the bottom of the U-shaped cutout 42 of second middle layer 40.

Preparation of Reagents 1 & 2

Reagents 1 and 2 comprise the oxidized form of a redox mediator, a stabilizer, a binder, a surfactant, and a buffer. Reagent 2, in addition, contains an enzyme. The oxidized form of the redox mediator, potassium ferricyanide, was found to be stable in the matrices. The quantity used in the formulation must be sufficient to attain a workable linear range. The enzyme must also have sufficient activity, purity and stability. A commercially available glucose oxidase may be obtained from Biozyme, San Diego, Calif. as Cat. No. G03A, about 270 U/mg. The stabilizer must be sufficiently water-soluble and be capable of stabilizing both the mediator and the enzyme. The binder should also be capable of binding all other chemicals in the reagents in electrode areas W1, W2 and R to the conductive surface/layer 21 of base layer 20. The preferred stabilizer is polyethylene glycol (Cat. No. P4338, Sigma Chemicals, St. Louis, Mo.). The preferred binder is Methocel 60 HG (Cat. No. 64655, Fluka Chemical, Milwaukee, Wis.). The buffer solution must have sufficient buffer capacity and pH value to optimize the enzyme reaction. A 0.05 M citrate buffer is preferred. The surfactant is necessary to facilitate dispensing of Reagents 1 and 2 into cutouts 32, 34 and 36 of middle layer 30 as well as for quickly dissolving the dry chemical reagents. The amount and type of surfactant is selected to assure the previously mentioned functions and to avoid a denaturing effect on the enzyme. The preferred surfactant is Triton X-100. The reagents are prepared as follows:

Reagent 1

Step 1: Prepare 50mM citrate buffer (pH 5.7) by dissolving 0.1512 grams citric acid and 1.2580 grams sodium citrate in 100 ml of deionized water.

Step 2: Prepare a 1% methocel 60HG solution by stirring 1 gram of methocel in 100 ml of citrate buffer from Step 1 for 12 hours.

Step 3: Add 0.3 ml of 10% Triton X-100 into the methocel solution.

Step 4: Add 2.5 grams of polyethylene glycol into the solution from Step 3.

Step 5: While stirring, add 1 gram of potassium ferricyanide to the solution from Step 4.

Reagent 2

Step 1–Step 4: same steps as Reagent 1.

Step 5: While stirring, add 6.5 grams potassium ferricyanide to the solution of Step 4.

Step 6: Add 1.0 gram of glucose oxidase to the solution of Step 5 and stir for 10 minutes or until all solid materials are completely dissolved.

Electrode Construction

A piece of a gold or tin oxide/gold polyester film available from Courtaulds Performance Films is cut to shape, as illustrated in FIG. 2, forming base layer 20 of sensor 10. A $CO_2$ laser was used to score the gold or tin oxide/gold polyester film. As illustrated in FIG. 2, the film was scored by the laser such that three electrodes at sample fluid end 110 and three contact points 122, 124 and 126 were formed at electrical contact end 120. The scoring line is very thin but sufficient to create three separate electrical conductors. A scoring line 28 can be made, but is not necessary, along the outer edge of base layer 20 to avoid potential static problems which could cause a noisy signal from the finished sensor 10.

A piece of one-sided adhesive tape is then cut to size and shape forming first middle layer 30 so that it will cover a majority of the conductive layer 21 of base layer 20 except for exposing a small electrical contact area illustrated in FIG. 1. Three rectangular, square or circular cutouts 32, 34 and 36 of substantially equal size are punched by $CO_2$ laser (25W laser available from Synrad, Inc., San Diego, Calif.). Cutouts 32, 34 and 36 define the electrode areas W1, W2 and R which hold chemical reagents. The size of the cutouts is preferred to be made as small as possible in order to make the fluid sample channel 112 of sensor 10 as short as possible while still being capable of holding sufficient chemical reagent to function properly. The preferred hole size for the present invention has a typical dimension of about 0.033 in. (0.84 mm) by about 0.043 in. (1.09 mm). As illustrated in FIG. 2, cutouts 32, 34 and 36 are aligned with each other and having a spacing of about 0.028 in. (0.71 mm) between them. The rectangular cutouts are for illustrative purposes only. It should be understood that the shape of the cutouts is not critical provided that the size of the cutouts is big enough to hold sufficient chemical reagents for the electrodes to function properly but small enough to allow for a reasonably small sample channel. As noted earlier, changing the shape of the cutouts or the surface area of the cutouts may require changing the constant values $k_1$–$k_5$ for Eq. 1 and Eq. 2. As stated previously, the preferred arrangement of the electrodes formed in cutouts 32, 34 and 36 is W1 (working electrode 1), R (reference electrode) and W2 (working electrode 2).

0.4 microliters of Reagent 1 is dispensed into electrode areas W1 and R. Reagent 1 is a mixture of a redox mediator, a stabilizer, a binder, a surfactant, and a buffer. The preferred mixture for Reagent 1 is made by mixing the following components in the described percentages (W/W %): about 1% potassium ferricyanide, about 2.5% polyethylene glycol, about 1% methocel 60 HG, about 0.03% Triton X-100 and about 0.05 M citrate buffer (pH 5.7). 0.4 microliters of Reagent 2 is dispensed into electrode area W2. Reagent 2 is a mixture similar to that of Reagent 1 but with the addition of an enzyme capable of catalyzing a reaction involving a substrate of the enzyme. The preferred enzyme is glucose oxidase. The preferred mixture for Reagent 2 is made by mixing the following percentages (W/W %) of the following ingredients: about 6.5% potassium ferricyanide, about 2.5% polyethylene glycol, about 1% methocel 60 HG, about 0.03% Triton X-100, about 0.05 M citrate buffer (pH 5.7), and about 1% glucose oxidase. After the addition of the reagents, the device was dried for about 2 minutes at 55° C. in an oven. After drying, a piece of double-sided tape available from Adhesive Research was fashioned into second middle layer 40 with U-shaped channel 42. Second middle layer 40 is then layered onto first middle layer 30. As mentioned earlier, this second middle layer 40 serves as a spacer and defines the size of the fluid sample channel 112. Its width and length is optimized to provide for a relatively quick moving fluid sample. The preferred size of U-shaped channel 42 is about 0.063 in. (1.60 mm) wide by about 0.248 in. (6.30 mm) long.

A piece of a transparency film (Cat. No. PP2200 or PP2500 available from 3 M) is fashioned into top layer 50. A rectangular vent hole 52 is made using the $CO_2$ laser previously mentioned. The preferred size of vent hole 42 is about 0.075 in. (1.91 mm) by about 0.059 in. (1.50 mm). Vent hole 52 is located approximately 0.130 in. (3.3 mm) from fluid end 110 of sensor 10. Top layer 50 is aligned and layered onto second middle layer 40 to complete the assembly, as illustrated in FIG. 1, of sensor 10.

Figure 3:
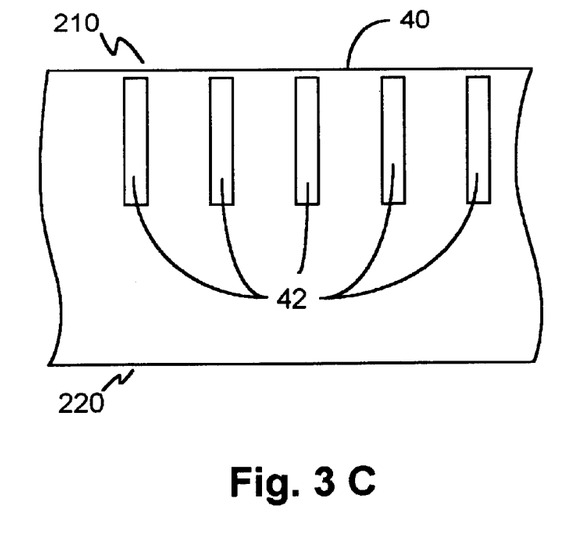
FIGS. 3A, 3B, 3C, and 3D are top views of a strip of each layer of the present invention showing the patterns for making multiple sensors of the present invention.
FIG. 3E is a top view of a segment of the laminated strip of the present invention showing the patterns for making multiple sensors of the present invention.
Figure 3A:
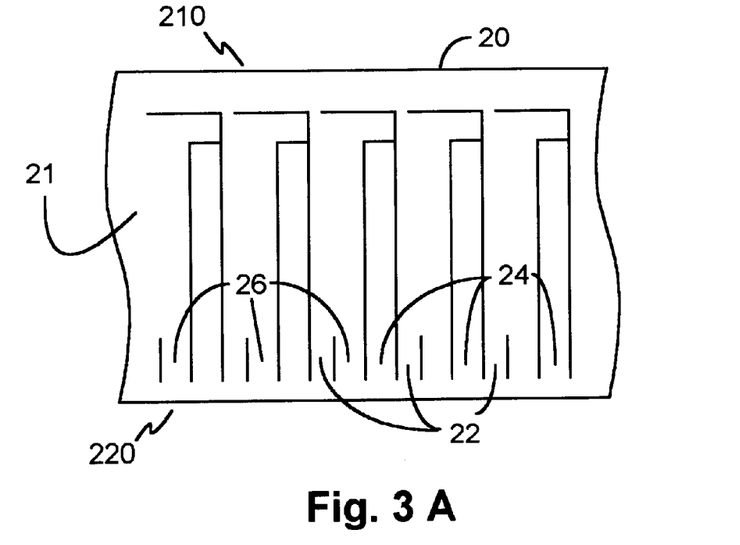
Figure 3B:
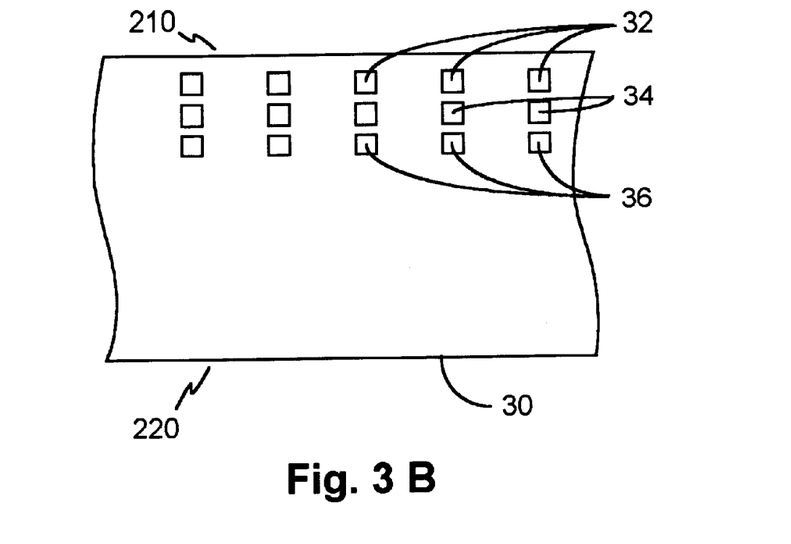
Figure 3E:
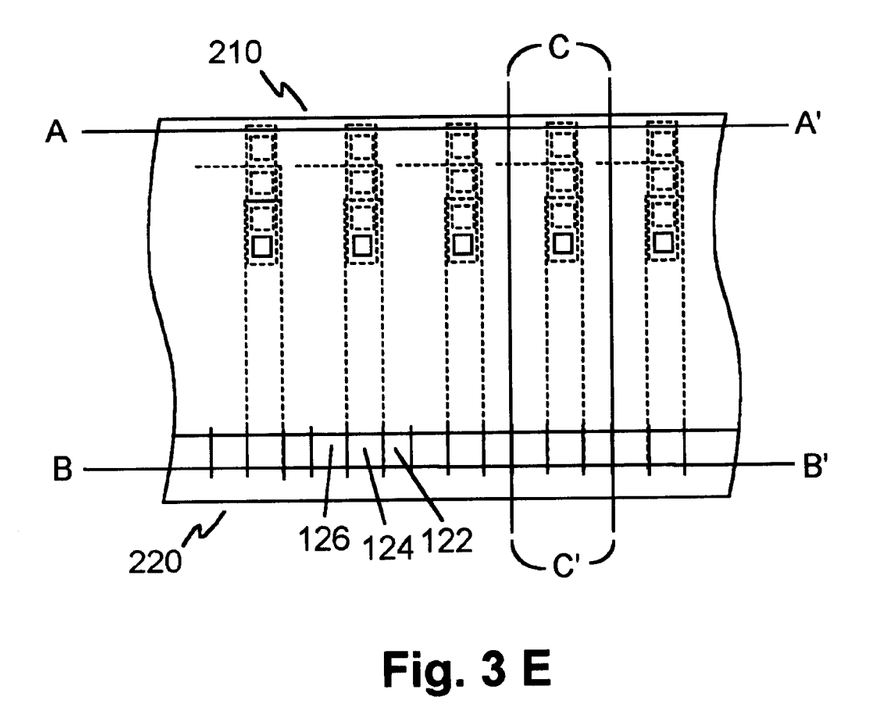

Although the description of electrode construction above describes construction for a single sensor, the design and materials used are ideal for making multiple sensors from one piece of each layer material as shown in FIGS. 3A–3E. This would be accomplished by starting with a relative large piece of base layer 20 having conducting layer 21 thereon. A plurality of scored lines are made into conductive layer 21 such that a repetitive pattern, as illustrated in FIG. 3A, is created using the preferred scribing method described previously whereby each pattern will eventually define the three conductive paths 22, 24 and 26 for each sensor. Similarly, a large piece of first middle layer 30, which is illustrated in FIG. 3B and which also has a plurality of cutouts 32, 34, and 36 in a repetitive pattern, is sized to fit over base layer 20 in such a way that a plurality of sensors 10 will be had when completed. The size of each cutout and the electrode material disposed in the plurality of electrode areas W1, R and W2 are similar to that disclosed above. After disposing Reagents 1 & 2 in their respective cutouts and dried, a large piece of second middle layer 40 having a plurality of elongated cutouts 42 and illustrated in FIG. 3C is layered onto first middle layer 30 such that each elongated cutout 42 of second middle layer 40 contains corresponding cutouts 32, 34 and 36 of first middle layer 30. A comparably-sized top layer 50 having a plurality of vent openings 52 in a repetitive pattern, as shown in FIG. 3D, is layered onto second middle layer 40. FIG. 3E is a top view of the combined layers. The laminated strip created by the four layers 20, 30, 40 and 50 has a plurality of sensors 10 that can be cut from the laminated strip. The laminated strip is cut longitudinally along line A–A' at fluid sampling end 210 to form a plurality of sampling apertures 114 and longitudinally along line B–B' at electrical contact end 220 to form a plurality of conductive contacts 122, 124 and 126. The laminated strip is also cut at predetermined intervals along line C–C' forming a plurality of individual sensors 10. Shaping of the fluid sampling end 120 of each sensor 10, as illustrated in FIG. 1, may be performed if desired. It should be understood by those skilled in the art that the order in which the laminated strip can be cut is not important. For instance, the laminated strip may be cut at the predetermined intervals (C–C') and then the cuts along A–A' and B–B' can be made to complete the process.

The following examples illustrate the unique features of the present invention which includes the compensation for varying hemotacrit levels by measuring sample fluid resistance and nullification of the interference effects of oxidizable species present in the sample fluid. All sensors of the present invention were tested on a breadboard glucose meter manufactured by Nova Biomedical Corporation of Waltham, Mass. A potential of 0.35 Volts was applied across the working electrodes and the reference electrode and the resultant current signals were converted to glucose concentrations in accordance with the disclosure of the present invention. The readings were compared to readings (control readings) obtained on the same samples using YSI Glucose Analyzer (Model 2300) available from Yellow Springs Instruments, Inc., Yellow Springs, Ohio.

EXAMPLE 1

Demonstration of Hematocrit Compensation

The unique design of the present invention makes it possible to measure the resistance of the fluid sample. This is achieved by applying the same reagent, Reagent 1, to the reference electrode R and the first working electrode W1. The chemical reagents used in Reagent 1 are critical for accurate measurement of the resistance. Reagent 1 can not contain a large amount of salts or any glucose oxidase. Otherwise, the resulting resistance would not be accurate and would be glucose dependent. For proper functioning of the present invention, it should be noted that a minimum amount of a mediator such as potassium ferricyanide for the reference electrode is essential.

Figure 4A:
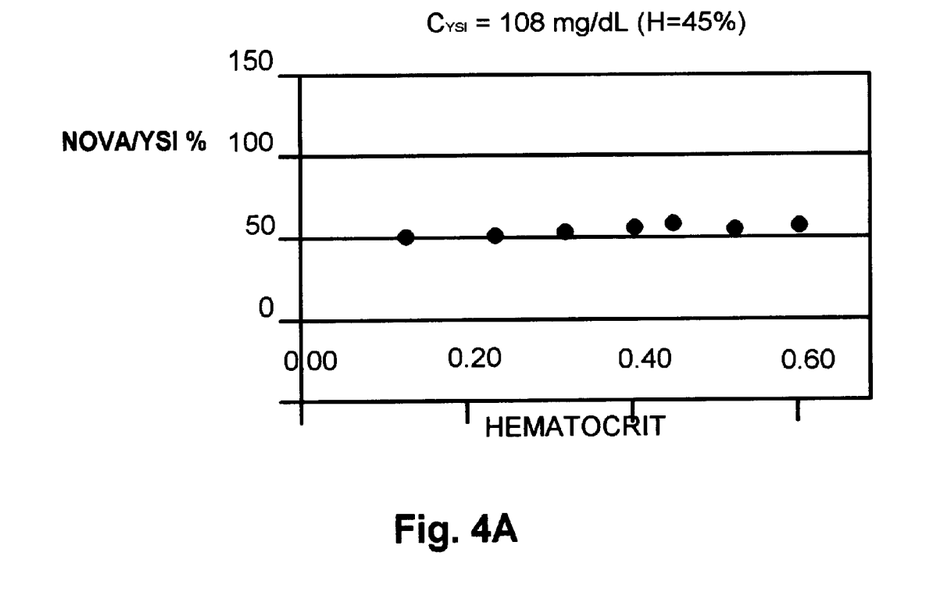
FIGS. 4A and 4B are graphs showing the effect of hematocrit on the concentration response of the present invention in normal and high concentrations of blood glucose.
Figure 4B:
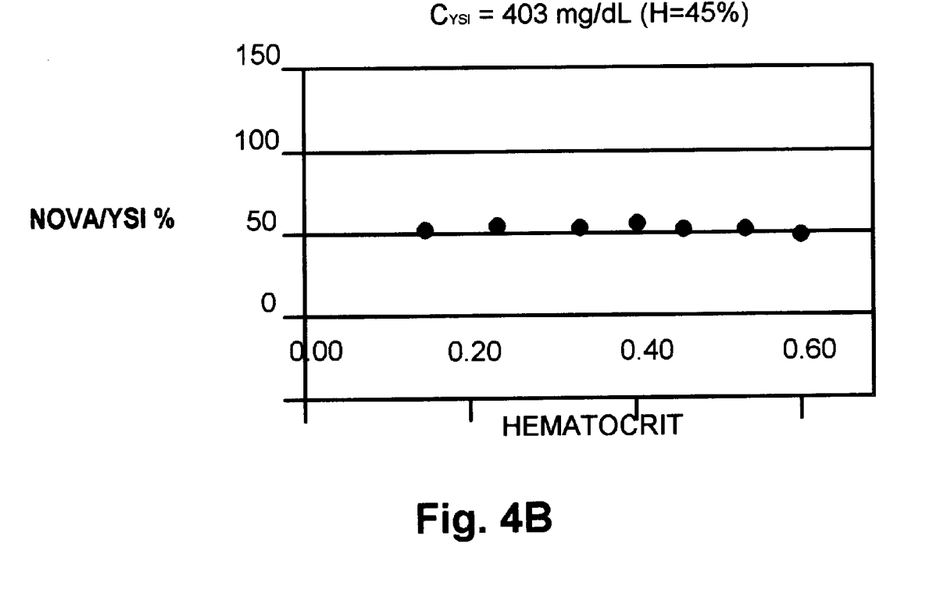

Resistance of a sample fluid, in this case blood samples, between W1 and R is measured at any time, preferably 20 seconds after a reading device (Nova glucose meter) is triggered by the blood samples. Blood samples with different hematocrit levels were prepared by spinning a whole blood sample and recombining plasma and red blood cells in varying ratios. Hematocrit levels were measured with a micro hematocrit centrifuge. Concentrations of glucose in the various samples were measured by sensors of the present invention ($C_{mea}$) and by a YSI blood glucose analyzer (the control), Model 2300, Yellow Springs Instruments, Inc., Yellow Springs, Ohio. Equations (1) and (2), previously mentioned, were used to calculate the corrected glucose concentration ($C_{corr}$) measured by sensors of the present invention to demonstrate the hemotacrit compensation feature of the present invention. The data obtained was plotted and FIGS. 4A and 4B show two graphs representing the percent correlation of the readings obtained using sensors of the present invention with the Nova glucose meter to the readings obtained for the samples using the YSI blood glucose analyzer at low and high levels of glucose in samples with varying hematocrit levels.

EXAMPLE 2

Demonstration of Interference Free Feature

The unique design of the present invention makes it possible to eliminate interference from oxidizable substances such as ascorbic acid, acetaminophen, uric acid, and other possible interferants present in the sample. This is achieved by subtracting the response obtained from W1 from the response obtained at W2, and is represented by the following equation:

$$I = Iw_2 - Iw_1 \qquad \text{Eq. (3)}$$

where $Iw_2$ is the current at W2 (second working electrode)

$Iw_1$ is the current at W1 (first working electrode)

I is the difference between W2 and W1 and represents the current due to oxidation of the mediator of its reduced form, which is proportional to the glucose concentration in the sample Because W1 and W2 have the same surface area, the potential interference present in the sample fluid should give relatively identical signals from each working electrode. Even though W1 and W2 had different reagents, it was found that there was no remarkable difference in the response to the interference. Thus, the difference in current response obtained in blood samples was due to the glucose present in the samples. This was tested by spiking normal and high glucose blood samples with 1 mM and 5 mM ascorbic acid, acetaminophen and uric acid. Table 1 shows the percentage response change of the readings obtained with sensors of the present invention and various commercially available sensors (referred to as Strip 1, Strip 2, Strip 3, and Strip 4) in blood samples having a concentration of 100 mg/dL glucose and 300 mg/dL upon addition of the interferents.

TABLE 1

Response change (%) Upon Addition of Interferent

| mM | Nova | Strip 1 | Strip 2 | Strip 3 | Strip 4 |
|---|---|---|---|---|---|
| 100 mg/dL glucose: ascorbic acid | | | | | |
| 0 | 0 | 0 | 0 | 0 | 0 |
| 1 | 4 | 26.7 | 19.8 | 21.3 | 6 |
| 5 | 4.5 | 133.6 | 115.8 | 151.5 | Error |
| 300 mg/dL glucose:ascorbic acid | | | | | |
| 0 | 0 | 0 | 0 | 0 | 0 |
| 1 | −0.9 | 7.2 | 14 | 14.7 | −4.3 |
| 5 | −0.5 | Hi | 107.3 | Hi | Error |
| 100 mg/dL glucose:acetaminophen | | | | | |
| 0 | 0 | 0 | 0 | 0 | 0 |
| 1 | 3.0 | 34.7 | 5* 7 | 50 | −8.2 |
| 5 | 3.4 | 90.8 | 38 | 136 | −13.4 |
| 300 mg/dL glucose:acetaminophen | | | | | |
| 0 | 0 | 0 | 0 | 0 | 0 |
| 1 | −3.4 | 20 | 3.5 | 18 | −7.2 |
| 5 | −3.5 | 39 | 8.0 | 23.7 | −17.5 |
| 100 mg/dL glucose:uric acid | | | | | |
| 0 | 0 | 0 | 0 | 0 | 0 |
| 1 | −2.7 | 32 | 35 | 35 | −1.3 |
| 300 mg/dL glucose:uric acid | | | | | |
| 0 | 0 | 0 | 0 | 0 | 0 |
| 1 | −4.5 | 10 | 15 | 7 | −1 |

From the test data, one observes that the readings obtained from sensors of the present invention show essentially no change in the presence of 1 mM and 5 mM ascorbic acid and acetaminophen, and 1 mM uric acid. All commercially available sensors except one, Strip 4, suffer from serious interference. Strip 4 showed an "error" for 5 mM ascorbic acid. At concentrations of 300 mg/dL glucose, sensors of the present invention also showed no interference (response change of less than 5%) upon spiking the samples with 1 mM and 5 mM ascorbic acid. The commercially available sensors showed about 7% to about 15% response increase for 1mM ascorbic acid spiked samples, and showed a "Hi" reading for 5 mM ascorbic acid spiked samples. Strip 4 again showed an "error" for 5 mM ascorbic acid spiked samples. In samples containing acetaminophen and uric acid, all commercially available strips showed varying degrees of error except for Strip 4 in samples containing uric acid.

EXAMPLE 3

Demonstration of Minimum Sample Volumes Feature

Figure 5:
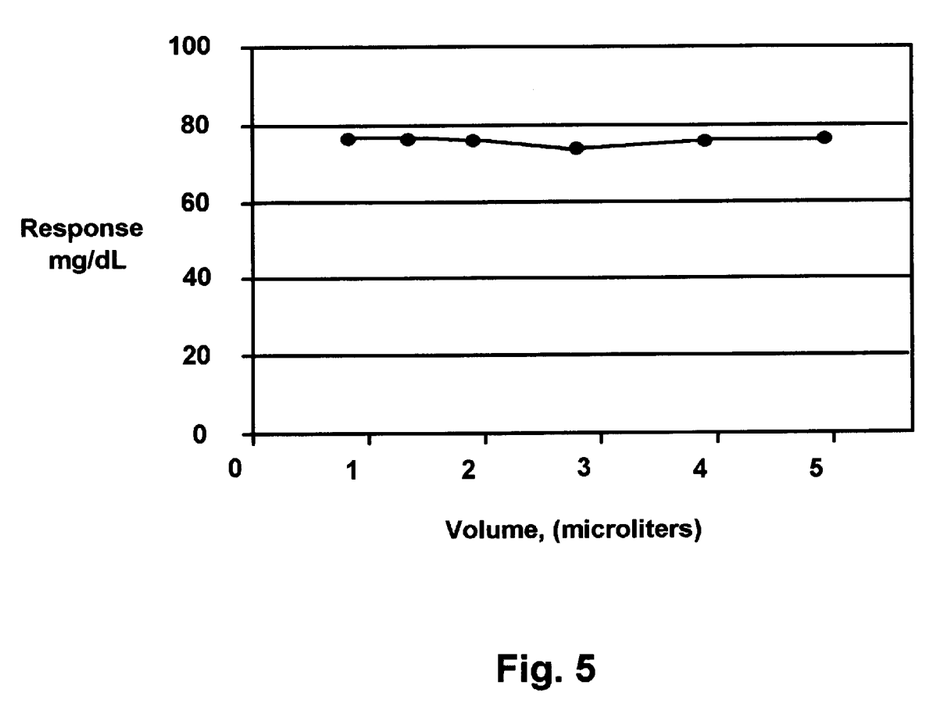
FIG. 5 is a correlation of sample volume on the concentration response of the present invention.

The unique design of the present invention enables the measurement of sample sizes smaller than which have heretofore been possible. Blood samples are applied to the sensors and the samples travel along the fluid sample channel to the venting hole. The blood volume required for measurement of blood glucose is determined by the channel volume. The calculated volume for the present invention is 1.44 microliters. In order to test the volume effect on sensor response, different blood sample volumes were applied to the sensors and the resulting concentration readings were plotted against volume. The test data is shown in FIG. 5.

Sensors of the present invention show no dependence of the response on the sample volume if the volume is above 1.5 microliters. It was found that sensors of the present invention still gave reasonable readings on sample sizes as low as 1.0 microliters. This is possible because the hydrophilic character of Reagent 1 applied to W1 and R, and Reagent 2 applied to W2 permitted the sample to cover the electrode areas even though the blood volume did not fill the entire sample channel.

EXAMPLE 4

Demonstration of Wide Linear Range and Precision Feature

Figure 6:
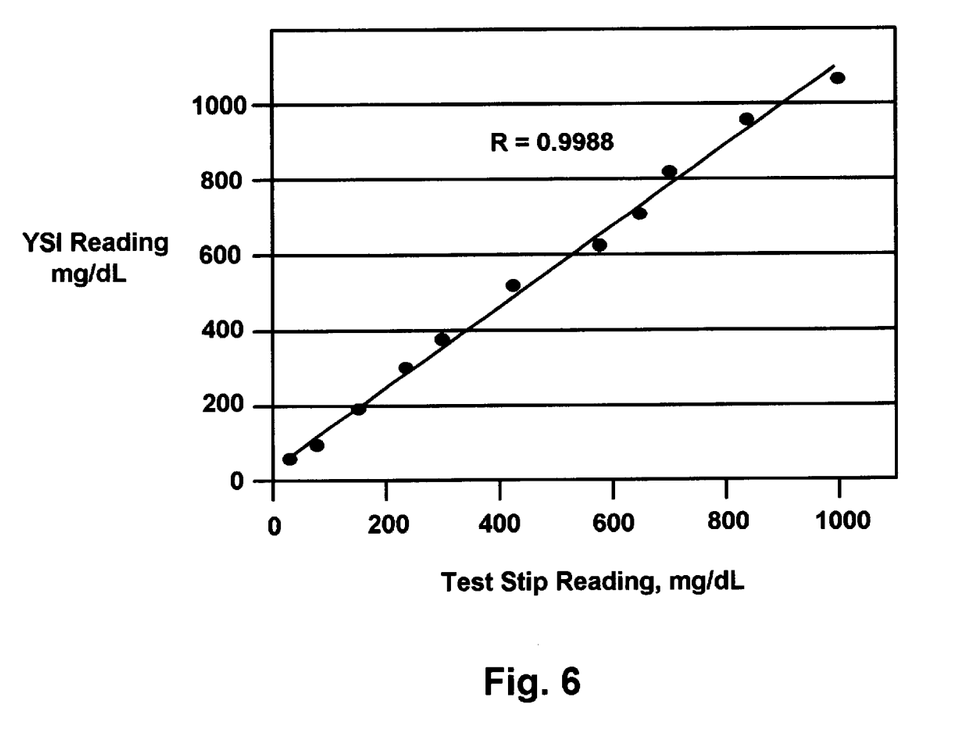
FIG. 6 is a correlation curve of the concentration readings using sensors of the present invention versus the concentration readings of obtained on the same samples using a YSI glucose analyzer.

A sample of venous blood was collected and separated into several aliquots. Each aliquot was spiked with different glucose concentrations ranging from 35 to 1000 mg/dL. The aliquots were each measured with a YSI glucose analyzer and then with sensors of the present invention using the Nova glucose meter. Sensors of the present invention show a linear relationship of current response vs. glucose concentration from 35 to 1000 mg/dL. The concentration readings were plotted against the concentration values obtained using the YSI meter (the control) and are illustrated in FIG. 6.

A regression coefficient of 0.9988 indicated a near perfect match with the readings obtained with the YSI blood glucose analyzer. The same aliquots were tested using four different commercially-available sensors with their accompanying meters. The commercially-available sensors showed a linear response only up to about 600 mg/dL. Above the 500–600 mg/dL range, all commercially available sensors displayed "Hi" as the test result.

The precision of the sensors of the present invention was investigated at the same glucose level range from about 35 to 1000 mg/dL. Four different batches of sensors of the present invention were used in the precision tests. Typically, the relative standard deviation was about 9.5%, 5.0%, 3.5%, 2.9%, and 2.6% for samples containing 35, 100, 200, 500, and 1000 mg/dL levels of glucose, respectively.

What is claimed is:

1. A disposable electrode strip for testing a fluid sample comprising:

a laminated strip having a first strip end, a second strip end and a vent opening spaced from said first strip end, said laminated strip comprising a base layer with at least three electrodes delineated thereon, a reagent holding layer carried on said base layer, said reagent holding layer having at least three cutouts, a channel forming layer carried on said reagent holding layer, and a cover;

an enclosed channel between said first strip end and said vent opening, said enclosed channel containing said at least three cutouts;

a first reagent disposed in a first cutout of said at least three cutouts forming a reference electrode;

a second reagent disposed in a second cutout of said at least three cutouts forming a first working electrode, said second reagent being substantially similar to said first reagent;

a third reagent disposed in a third cutout of said at least three cutouts forming a second working electrode, said third reagent containing an enzyme; and conductive contacts at said second strip end and insulated from said enclosed channel.

2. The electrode strip of claim 1 wherein said enzyme is glucose oxidase.

3. The electrode strip of claim 1 wherein said first reagent, said second reagent and said third reagent contain a redox mediator.

4. The electrode strip of claim 3 wherein said first reagent, said second reagent and said third reagent further contain at least one of a stabilizer, a binder, a surfactant, and a buffer.

5. The electrode strip of claim 4 wherein said stabilizer is a polyalkylene glycol, said binder is a cellulose material, and said surfactant is a polyoxyethylene ether.

6. The electrode strip of claim 5 wherein said stabilizer is polyethylene glycol, said binder is methyl cellulose, said surfactant is t-octylphenoxypolyethoxyethanol, and said buffer is a citrate buffer.

7. The electrode strip of claim 6 wherein said first reagent and said second reagent are made of a mixture having starting components comprising about 1 wt % of said potassium ferricyanide, about 2.5 wt % of said polyethylene glycol, about 1 wt % of said methyl cellulose, about 0.03 wt % of said t-octylphenoxypolyethoxyethanol, and said citrate buffer is about 0.05M.

8. The electrode strip of claim 6 wherein said third reagent is made of a mixture having starting components comprising about 6.5 wt % of said potassium ferricyanide, about 2.5 wt % of said polyethylene glycol, about 1 wt % of said methyl cellulose, about 0.03 wt % of said t-octylphenoxypolyethoxyethanol, and said pH buffer is about a 0.05M citrate buffer, and about 1 wt % of said enzyme.

9. The electrode strip of claim 8 wherein said enzyme is glucose oxidase.

10. The electrode strip of claim 4 wherein said first reagent, said second reagent and said third reagent are made from a mixture having starting components comprising about 1 wt % to about 6.5 wt % of said redox mediator, about 2.5 wt % of said stabilizer, about 1 wt % of said binder, and about 0.03 wt % of said surfactant in said buffer.

11. The electrode strip of claim 10 wherein said citrate buffer is about 0.05M.

12. The electrode strip of claim 3 wherein said redox mediator is at least one metal complex.

13. The electrode strip of claim 3 wherein said at least one redox mediator is selected from the group consisting of potassium ferricyanide and other inorganic and organic redox mediators.

14. The electrode strip of claim 1 wherein said base layer has a conductive coating disposed thereon for forming said at least three electrodes.

15. The electrode strip of claim 14 wherein said conductive coating is gold.

16. The electrode strip of claim 14 wherein said conductive coating comprising gold and tin oxide.

17. The electrode strip of claim 14 wherein said base layer, said reagent holding layer, said channel forming layer, and said cover are made of a plastic dielectric material.

18. The electrode strip of claim 17 wherein said plastic material is selected from the group consisting of polyvinyl chloride, polycarbonate, polysulfone, nylon, polyurethane, cellulose nitrate, cellulose propionate, cellulose acetate, cellulose acetate butyrate, polyester, acrylic, and polystyrene.

19. The electrode strip of claim 1 wherein said enclosed channel is hydrophilic.

20. The electrode strip of claim 1 wherein said enclosed channel has a volume of about 1.44 microliters.

21. The electrode strip of claim 1 wherein said cover has a hydrophilic coating on at least one side.

22. The electrode strip of claim 1 wherein said channel forming layer has a thickness sufficient to optimize the flow of said fluid sample along said open path.

23. The electrode strip of claim 22 wherein said thickness is about 0.007 inches (0.1778 mm).

24. The electrode strip of claim 1 wherein the surface area of said first working electrode is substantially same as the surface area of said second working electrode.

25. A method of using an electrode strip for determining the concentration of an analyte, said electrode strip having a first working electrode, a second working electrode and a reference electrode wherein said first working electrode contains an enzyme capable of catalyzing a reaction involving a substrate for the enzyme, said first working electrode, said second working electrode and said reference electrode being disposed in a fluid sample channel for measuring a fluid sample, said method comprising:

disposing said fluid sample into said channel of said electrode strip;

applying a potential between said reference electrode and said first working electrode which contains said enzyme;

measuring a first current generated between said first working electrode and said reference electrode and correlating said first current to a concentration of said analyte in said fluid sample;

measuring a resistance value of said fluid sample between said second working electrode and said reference electrode;

applying said resistance value to a first equation and determining the hematocrit level of said fluid sample; and calculating a corrected concentration of said analyte using a second equation to correct for the presence of hematocrit in said sample.

26. The method of claim 25 wherein said method further comprising:

applying a potential between said reference electrode and said second working electrode;

measuring a second current generated between said second working electrode and said reference electrode;

subtracting said second current from said first current and obtaining a current difference, correlating said current difference to a concentration of said analyte in said fluid sample.

27. The method of claim 26 wherein said method further includes triggering said current measuring step when said fluid sample contacts said first working electrode, said second working electrode and said reference electrode creating said first current and said second current.

28. The method of claim 27 wherein said method further includes reading a current value for each of said first current and said second current at about a time where said current values for each of said first current and said second current reach a steady-state.

29. The method of claim 28 wherein said reading is taken at about 20 seconds after said current measuring step is triggered.

30. A disposable electrode strip for detecting or measuring the concentration of at least one analyte in a fluid sample, said electrode strip comprising:

an insulating base strip having a first base end and a second base end;

a conductive layer disposed on one side of said base strip delineating at least three electrically-distinct conductive paths insulated from each other;

a first electrical insulator sized smaller than said insulating base strip and overlaying a substantial portion of said conductive layer, said first insulator having at least a first cutout portion and a second cutout portion spaced from said first base end, said first cutout portion exposing a limited area of a first of said at least three conductive paths and said second cutout portion exposing a limited area of a second and a third of said at least three conductive paths;

at least two electrode materials wherein a first material of said at least two electrode materials is a reagent for measuring the concentration of said at least one analyte and wherein a second material of said at least two electrode materials is a material suitable for use as a reference material and for measuring the resistance of said fluid sample, said first material being disposed in said first cutout potion and said second material being disposed in said second cutout portion, said second material being scored to isolate said second material disposed on said second of said at least three conductive paths from said second material disposed on said third of said at least three conductive paths; and a second electrical insulator sized to fit over and coextensive with said first electrical insulator, said second insulator having an opening configured to expose an area of said first insulator a limited distance from said first base end of said insulating base strip, said area including said at least two cutout portions of said first insulator; and a third electrical insulator sized to fit over and coextensive with said second insulator creating a sample fluid channel, said third insulator having a third insulator vent aperture spaced from said first base end and configured to expose at least a small portion of said opening of said second insulator.

31. The strip of claim 30 wherein said sample fluid channel has a volume of 1.44 microliters.

32. The strip of claim 30 wherein said sample fluid channel is hydrophilic.

33. The device of claim 30 wherein said first material and said second material are mixtures having starting components comprising a redox mediator, a stabilizer, a binder, a surfactant, and a buffer.

34. The strip of claim 33 wherein said redox mediator is at least one metal complex selected from the group consisting of ferrocene, ferrocene derivatives and potassium ferricyanide, said stabilizer is a polyalkylene glycol, said binder is a cellulose material, said surfactant is a polyoxyethylene ether, and said buffer has a pH of about 5 to about 6.

35. The strip of claim 34 wherein said mediator is potassium ferricyanide, said stabilizer is polyethylene glycol, said binder is methyl cellulose, said surfactant is t-octylphenoxypolyethoxyethanol, and said buffer is a citrate buffer.

36. The strip of claim 35 wherein said first material is made of a mixture having starting components comprising about 1 wt % of said potassium ferricyanide, about 2.5 wt % of said polyethylene glycol, about 1 wt % of said methyl cellulose, and about 0.03 wt % of said t-octylphenoxypolyethoxyethanol in said citrate buffer.

37. The strip of claim 35 wherein said second material is made of a mixture having starting components comprising about 6.5 wt % of said potassium ferricyanide, about 2.5 wt % of said polyethylene glycol, about 1 wt % of said methyl cellulose, about 0.03 wt % of said t-octylphenoxypolyethoxyethanol, and about 1 wt % of an enzyme in said citrate buffer.

38. The strip of claim 37 wherein said enzyme is glucose oxidase.

39. The strip of claim 30 wherein said insulating base strip, said first electrical insulator, said second electrical insulator, and said third electrical insulator are made from a plastic material selected from the group consisting of polyvinyl chloride, polycarbonate, polysulfone, nylon, polyurethane, cellulose nitrate, cellulose propionate, cellulose acetate, cellulose acetate butyrate, polyester, acrylic, and polystyrene.

40. A method of making multiple, disposable sensors wherein each sensor has a first working electrode, a second working electrode and a reference electrode, wherein said first working electrode contains an enzyme capable of catalyzing a reaction involving a substrate for the enzyme, said first working electrode, said second working electrode and said reference electrode being disposed in a fluid sample channel for measuring a fluid sample, said method comprising:

obtaining a base strip of an insulating material having a layer of conductive material disposed thereon, said base strip having a first edge and a second edge;

scribing in said conductive material a plurality of lines in a repetitive pattern wherein said plurality of lines contain a repetitive pattern forming three conductive paths in each of said repetitive pattern;

disposing a first middle layer of insulating material over said base strip, said first middle layer having a repetitive pattern of three cutouts wherein each cutout of each of said repetitive pattern exposes an electrode portion of each of said three conductive paths of each repetitive pattern wherein said repetitive pattern of said three cutouts are spaced from said first edge of said base strip, and wherein said first middle layer is sized to expose a contact portion of each of said three conductive paths of each repetitive pattern for a distance from said second edge of said base strip;

disposing a first reagent material on two of said three cutouts of each repetitive pattern and a second reagent material on the other of said three cutouts of each repetitive pattern;

drying said first reagent material and said second reagent material;

overlaying a second middle layer of insulating material over and coextensive with said first middle layer; said second middle layer having a plurality of elongated cutout portions in a repetitive pattern wherein each of said elongated cutout portions exposes a corresponding repetitive pattern of said three cutouts said first middle layer;

disposing a top layer of insulating material over and coextensive with said second middle layer, said top layer having a plurality of vent openings in a repetitive pattern wherein each of said vent openings exposes a portion of a corresponding repetitive pattern of said elongated cutout portion furthest from said first edge of said base strip; and separating each of said repetitive pattern forming one of each of said disposable sensors.

41. The method of claim 40 further comprising drying said first reagent material and said second reagent material at a temperature and for a length of time sufficient to allow said first reagent material and said second reagent material to solidify and adhere to each of said electrode portion of each of said repetitive pattern of said three conductive paths.

42. The method of claim 40 further comprising cutting along said first edge of each of said sensors and transverse to said sensors a predetermined distance creating a sample inlet port.

* * * * *